United States Patent [19]

Kihara et al.

[11] Patent Number: 4,614,821
[45] Date of Patent: Sep. 30, 1986

[54] METHOD OF PRODUCING 1,2,3-TRITHIANE COMPOUNDS

[75] Inventors: Kazuaki Kihara; Makoto Kuroda, both of Hikari, Japan

[73] Assignee: Takeda Chemical Industries, Ltd., Osaka, Japan

[21] Appl. No.: 819,483

[22] Filed: Jan. 16, 1986

Related U.S. Application Data

[63] Continuation of Ser. No. 666,101, Oct. 29, 1984, abandoned.

[30] Foreign Application Priority Data

Oct. 28, 1983 [JP] Japan ................................. 58-203146

[51] Int. Cl.⁴ .................. C07D 341/00; C07D 409/04; C07D 413/04
[52] U.S. Cl. .................................... 544/145; 544/374; 546/207; 548/146; 548/527; 549/19
[58] Field of Search ................ 544/145, 374; 546/207; 548/146, 527; 549/19; 568/26, 21

[56] References Cited

FOREIGN PATENT DOCUMENTS 2039666  2/1971  Fed. Rep. of Germany .
136689  11/1976  Japan .
127387  10/1980  Japan .
544037  12/1973  Switzerland .

OTHER PUBLICATIONS

Kharasch et al., The Chemistry of Organic Sulfur Compounds, vol. 2, pp. 367–402 (1966).

*Primary Examiner*—Robert W. Ramsuer
*Attorney, Agent, or Firm*—Wenderoth, Lind & Ponack

[57] ABSTRACT

This invention relate to a process for producing a 1,2,3-trithiane compound of the general formula:

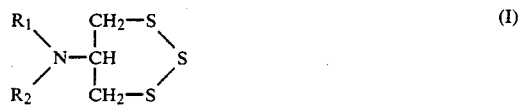

(I)

wherein each of $R_1$ and $R_2$ is independently a lower alkyl group, or alternatively, $R_1$ and $R_2$ together with the adjacent nitrogen atom form a 5- or 6-membered heterocyclic group which may further contain an oxygen, sulfur or nitrogen atom, or a salt thereof, which comprises reacting a compound of the general formula:

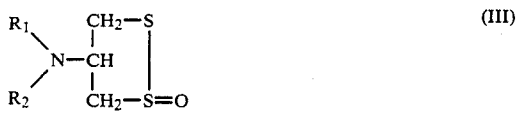

(III)

wherein $R_1$ and $R_2$ are as defined above, or a salt thereof with a compound of the general formula:

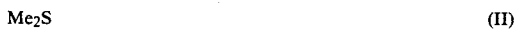

$Me_2S$ (II)

wherein Me is hydrogen, an alkali metal atom or an ammonium radical under an acid condition.

The compound (I) or a salt thereof is produced in high purity and high yield.

3 Claims, No Drawings

METHOD OF PRODUCING 1,2,3-TRITHIANE COMPOUNDS

This application is a continuation of now abandoned application Ser. No. 666,101, filed Oct. 29, 1984.

This invention relates to a method of producing 1,2,3-trithiane compounds which have insecticidal, nematocidal and fungicidal activities and are of value as an agricultural chemical, particularly as a pesticide. More particularly, this invention relates to a method of producing a 1,2,3-trithiane compound of the general formula:

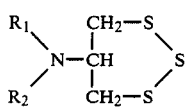

wherein each of $R_1$ and $R_2$ is independently a lower alkyl group, or alternatively, $R_1$ and $R_2$ together with the adjacent nitrogen atom form a 5- or 6-membered heterocyclic group which may further contain an oxygen, sulfur or nitrogen atom, or a salt thereof, which comprises reacting a compound of the general formula:

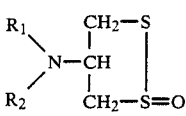

wherein $R_1$ and $R_2$ are as defined above, or a salt thereof with a compound of the general formula:

wherein Me is hydrogen, an alkali metal atom or an ammonium radical, under an acid condition.

The objective compound (I) of this invention is known in the literature. The compound (I) which shows insecticidal, nematocidal and fungicidal activities is described, for example, in Japanese Examined Published Patent Application Nos. 10596/1975, and 34110/1975 (these correspond to German Laid-Open Patent Application No. 2039666), Japanese Unexamined Published Patent Application Nos. 136689/1976 and 127387/1975, and Swiss Patent No. 544037.

However, processes of producing the compound (I) described in these literature references have the drawbacks that the yield of the objective compound is low, while by-products are formed in relatively large quantities, and are unsatisfactory for industrial production.

The present inventors conducted intensive study to develop a method of producing the compound (I) in higher yield, in higher purity, and with greater ease. As the result, the present inventors found that the compound (III) unexpectedly reacts with the compound (II) and one sulfur atom is thereby inserted in the 1,2-dithiolane ring of compound (III) and at the same time the <S=O (sulfoxide) bond is reduced, whereby the 1,2,3-trithiane compound (I) is produced in high purity and high yield. Further investigations based on the above finding have led to completion of this invention.

According to the method of this invention, the compound (I) can be produced in higher yield, in higher purity, and with greater ease.

Further, the main by-product in the reaction of this invention is a dithiolane compound of the general formula:

wherein $R_1$ and $R_2$ are as defined above.

The compound (IV) is easily oxidized with an oxidizing agent to give the compound (III) in high yield, as mentioned in detail hereinafter. The reactions can be represented as follows:

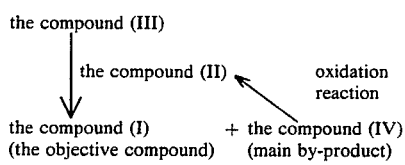

Thus, the by-product compound (IV) formed in the reaction of this invention can be easily converted into the starting compound (III) of the method of this invention, and by repeated conversion of the resulting by-product compound (IV) into the starting compound (III), the yield of the compound (I) can be made higher so as to amount to ca. 90-95%.

Referring to the above general formulas, each of $R_1$ and $R_2$ is independently a straight-chain or branched lower alkyl group containing 1 to 4 carbon atoms, such as methyl, ethyl, n-propyl, isopropyl, n-butyl, isobutyl, sec-butyl or tert-butyl, or alternatively, $R_1$ and $R_2$ together with the adjacent nitrogen atom form a 5- or 6-membered heterocyclic group which may further contain an oxygen, sulfur or nitrogen atom, such as pyrrolidino, piperidino, piperazino, morpholino or thiazolidinyl.

Among these, preferred are cases where each of $R_1$ and $R_2$ is independently a straight-chain or branched lower alkyl group containing 1 to 4 carbon atoms. More preferably, each of $R_1$ and $R_2$ is methyl.

As the salt of the compound (I) of this invention, use is made of an agriculturally acceptable salt thereof, such as an acid addition salt with an inorganic acid, e.g. hydrochloric acid, hydrobromic acid, sulfuric acid or phosphoric acid, or an organic acid, e.g. benzenesulfonic acid, p-toluenesulfonic acid, oxalic acid, acetic acid or maleic acid.

The compound (I) or a salt thereof is produced by reacting the compound (II) with the compound (III) or a salt thereof under an acid condition, namely at pH 5 or below, preferably pH 1 to 4.

As the salt of the starting compound (III), use is made of an acid addition salt with a conventional acid in the art, e.g. an inorganic acid, such as hydrochloric acid, hydrobromic acid, sulfuric acid or phosphoric acid; or an organic acid, such as benzenesulfonic acid, p-toluenesulfonic acid, oxalic acid, acetic acid or maleic acid. The starting compound (III) or a salt thereof, may exist in four kinds of stereoisomers due to the presence of an asymmetric carbon atom and a >S=O (sulfoxide) bond in the molecule. These four stereoisomers may be used after separating into individual optically active isomers or as a mixture of such optically active isomers.

As the starting compound (II) use is made of, for example, hydrogen sulfide, sodium sulfide, potassium sulfide or ammonium sulfide, preferably hydrogen sulfide or sodium sulfide.

In this reaction, the starting compound (II) may be used in an amount of about 0.8 to 3 moles per mole of starting compound (III) or a salt thereof.

In order to maintain the pH value of the reaction mixture in the acid range, namely at 5 or below, use is made of, for example, an inorganic acid, such as hydrochloric acid, hydrobromic acid, sulfuric acid or phosphoric acid; or an organic acid, such as benzenesulfonic acid, p-toluenesulfonic acid, oxalic acid or maleic acid.

The acid is generally used in such an amount as to maintain the pH value of the reaction mixture at 5 or below. For example, in the case of the reaction in water or a mixed solvent of water and an organic solvent, mentioned below, it is desirable to add the acid in small portions with the progress of reaction in such a manner as the pH value of the reaction mixture can be maintained in the acid region, namely at pH 5 or below, preferably in the range of pH 1 to 4.

The reaction is generally carried out in an inert solvent. Any solvent incapable of disturbing the reaction can be used. Use is made of, for example, water or an organic solvent, preferably water-miscible solvent, such as acetic acid, lower alcohols containing 1 to 3 carbon atoms, e.g. methyl alcohol, ethyl alcohol or isopropyl alcohol, acetone, acetonitrile, dimethylformamide or dimethyl sulfoxide alone, or as a mixture of the two or more solvents. Among these is water is preferred.

The reaction temperature is about $-20°$ C. to room temperature (about $15°$ C.), preferably about $-10°$ C. to $10°$ C. The reaction time depends on the reaction temperature and other factors, but generally is about 30 minutes to 4 hours.

The thus obtained compound (I) or a salt thereof is isolated and purified by a per se known procedure such as distillation, distillation under reduced pressure, solvent extraction, pH adjustment, solvent transformation, concentration, concentration under reduced pressure, crystallization, recrystallization or/and chromatography.

More concretely, after completion of the reaction using water as the reaction solvent, an organic solvent immiscible with water, such as ether, chloroform or benzene, is added to the reaction mixture, followed by neutralization with an appropriate alkali (e.g. alkali metal hydroxide, such as sodium hydroxide or potassium hydroxide) and separation of the organic layer. When the reaction is conducted in a mixed solvent of water and water-miscible organic solvent, after completion of the reaction the reaction mixture is concentrated under reduced pressure to remove the water-miscible organic solvent and then treated in the above manner. The organic layer obtained is concentrated under reduced pressure and the residue is purified by silica gel column chromatography to give the compound (I).

In this chromatography, the by-product compound (IV) can be easily isolated according to the method which is conventional per se and the compound (IV) may be converted into the starting compound (III) as described below.

Furthermore, the compound (I) may be isolated in the form of a salt by adding a solution of an acid, such as oxalic acid or hydrochloric acid, in a solvent, such as ether or benzene to the compound (I) isolated above according to a conventional procedure known per se.

In case that a mixture of the compounds (I) and (IV) is obtained, a solution of oxalic acid in a solvent, such as ethanol is added to the mixture, followed by filtering out the precipitated oxalate of compound (IV) to give the filtrate containing compound (I).

The thus obtained oxalate of compound (IV) can be converted back into the compound (III) according to the method described below.

The starting compound (III) or a salt thereof can be produced by a per se known method, for example, the method described in Agricultural and Biological Chemistry, 34, 30 935-940 (1970). Thus, the compound (III) or a salt thereof is produced by oxidizing the compound (IV), or a salt thereof, with an oxidizing agent under an acid condition. The examples of salt of compound (IV) include a salt with a conventional acid, e.g. an inorganic acid, such as hydrochloric acid, sulfuric acid or hydrobromic acid, or an organic acid, such as maleic acid, oxalic acid, fumaric acid, benzenesulfonic acid or p-toluenesulfonic acid.

As the oxidizing agent in the above reaction, use is made of, for example, organic and inorganic peracids. Examples of the peracid include among others, an organic peracid such as percarboxylic acids, e.g. performic acid, peracetic acid, trifluoroperacetic acid, permaleic acid, perbenzoic acid, m-chloroperbenzoic acid or monoperphthalic acid; or a persulfonic acid e.g. p-toluenepersulfonic acid, and an inorganic peracid, such as hydrogen peroxide, periodic acid or persulfuric acid. These peracids are used either singly or in a mixture of two or more according to the method which is known per se. Among these is hydrogen peroxide is preferred. The oxidizing agent is generally used in an amount of at least equivalent to the starting compound (IV), preferably in an amount of about 1.1 to 1.2 moles per mole of the compound (IV). The oxidation reaction is generally carried out in an inert solvent. The solvent is selected depending on the solubility of starting material and the kind of oxidizing agent. As the solvent, dichloromethane, chloroform, dimethylformamide, tetrahydrofuran, acetonitrile, water, acetic acid, ethyl acetate and the like solvents are generally used either solely or as a mixture of two or more solvents. Among the above-mentioned solvents water and acetic acid are preferred.

The reaction temperature is about $-10°$ C. to $60°$ C., preferably about $0°$ C. to $40°$ C. The reaction time is about 1 to 4 hours.

As the by-product, the unreacted compound (IV) is obtained, which can be used again as the starting compound in the oxidation reaction for the production of the compound (III).

After the conclusion of the reaction using, for example, water or a mixture of water and an organic solvent as the reaction solvent, the reaction mixture can be used in the subsequent reaction, as such and also after adding an organic solvent immiscible with water, such as benzene, chloroform or ether, neutralizing the resultant mixture with an aqueous solution of a suitable alkali (e.g., sodium hydroxide, potassium hydroxide, etc.) under cooling and concentrating the organic layer separated from the resulting two aqueous and organic layers to isolate the compound (III) as a free base form. Furthermore, the compound isolated by the above procedure may be made into a salt with a conventional acid, e.g. an inorganic acid, such as hydrochloric acid, sulfuric acid or hydrobromic acid; or an organic acid, such as maleic acid, oxalic acid, fumaric acid or p-toluenesulfonic acid, according to a per se conventional method, and then may be used in the subsequent reaction.

The starting compound (IV) can be produced by a known method, e.g. the method described in Agr. Biol. Chem., 34, 935(1970).

Thus, the compound (IV) can be produced according to the following reaction scheme.

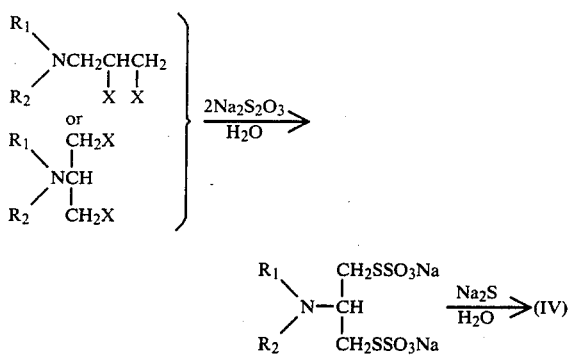

In above general formulas, X is a halogen such as chlorine or bromine; $R_1$ and $R_2$ are as defined above.

The thus obtained starting compounds are isolated and purified by means known per se, such as distillation, distillation under reduced pressure, solvent extraction, pH adjustment, solvent-transformation, crystallization, recrystallization or/and chromatography. This invention is illustrated by the following non-limiting examples.

The term "%" means weight % unless otherwise specified.

In the examples, the NMR spectra are measured at 60 MHz (solvent: d-trifluoroacetic acid) and expressed as $\tau$ value, whereby the symbols used herein have the following respective meanings: s, singlet; d, doublet; t, triplet; qr, quartet; ABqr, AB pattern quartet; qn, quintet; m, multiplet; J, coupling constant.

REFERENCE EXAMPLE 1

Production of
4-(N,N-dimethylamino)-1,2-dithiolane-1-oxide hydrochloride

To a 47.8 g of 4-(N,N-dimethylamino)-1,2-dithiolane oxalate is added 200 ml of water. To the resulting solution is added 75 ml of benzene. The mixture is neutralized by adding 35 ml of 28% aqueous sodium hydroxide with stirring while maintaining the mixture at a temperature of about 25° C. The neutralized mixture is filtered to thereby separate it into crystals and a filtrate. The crystals are washed well with a further 25-ml portion of benzene. The washings and the filtrate are combined. An aqueous layer is separated, and the benzene layer is extracted with 58 ml of 15% hydrochloric acid. The aqueous extract and the above aqueous layer are combined. Thereto is added dropwise 22 g of 30% aqueous hydrogen peroxide over about an hour while maintaining the aqueous solution at a temperature of 10° C. with stirring. After the addition, the reaction mixture is stirred for an hour. High performance liquid chromatographic analysis of this solution shows that the content of the title compound is 39.6 g (yield 98%). The reaction solution is almost concentrated to dryness under reduced pressure, and after 150 ml of ethanol is added to the residue to bring into a slurry form, the powder obtained by filtration is dried to give 34.3 g (yield of 85%) of the title compound.

IR: $\nu_{max}^{KBr}$cm$^{-1}$ 1078.
UV: $\lambda_{max}^{H_2O}$ m$\mu$241.
NMR: 5.7–6.5(5H,m), 6.92(6H,s).
m.p. 152.5°–167° C. (decomp.).

The following compounds are produced in the same manner as above:

4-(N,N-Diethylamino)-1,2-dithiolane-1-oxide hydrochloride
IR $\nu_{max}^{KBr}$cm$^{-1}$ 10800.
NMR 5.52(1H,qn), 6.48(4H,d,J=5.5 Hz), 6.56(4H,qr),
8.47(6H,t,J=7.0Hz).

4-(N,N-Methylethylamino)-1,2-dithiolane-1-oxide hydrochloride
IR $\nu_{max}^{KBr}$cm $^{-1}$ 1085.
NMR 5.56(1H,qn), 6.44(4H,d,J=6.0Hz), 6.65(2H,qr), 7.05(3H,s). 8.62(3H,t,J=7.0Hz).

4-(N,N-Methylcyclohexylamino)-1,2-dithiolane-1-oxide hydrochloride
IR $\nu_{max}^{KBr}$ $^{-1}$ 1087.
NMR 5.52(1H,m), 6.38(4H,d,J=7.0Hz), 6.59(1H,m), 6.93(3H,d,J=5.0Hz) 7.5–8.5(10H,m).

4-(N,N-Dicyclohexylamino)-1,2-dithiolane-1-oxide hydrochloride
IR $\nu_{max}^{KBr}$ cm$^{-1}$ 1093.
NMR 5.55(1H,m), 6.40(4H,d,J=6.5 HZ), 6.90(2H,m), 8.0 ∝ 9.2(20H,m).

4-(N,N-Piperidino-1,2-dithiolane-1-oxide hydrochloride
IR $\nu_{max}^{KBr}$ cm$^{-1}$ 1095.
NMR 5.58(1H,m), 6.46(4H,d,J=5.5 Hz), 5.9-7.1(4H,m), 7.98(6H,m).

4-(N,N-Morpholino)-1,2-dithiolane-1-oxide hydrochloride
IR $\nu_{max}^{KBr}$ cm$^{-1}$ 1098.
NMR 5.58(1H,m), 5.70(4H,m), 6.24(4H,m) 6.43(4H,d,J=5.0Hz).

EXAMPLE 1

Production of 5-dimethylamino-1,2,3-trithiane oxalate

To 10.09 g (0.05 mole) of 4-(N,N-dimethylamino)-1,2-dithiolane-1-oxide hydrochloride prepared in Reference Example 1 is added 50 ml of water.

To the resulting solution is added dropwise an aqueous sodium sulfide solution (a solution of 12.01 g (0.05 mole) of sodium sulfide nonahydrate in 22.8 ml of water) over about an hour while maintaining the reaction temperature at 5° C. and the pH value of the reaction mixture at 2 to 3 by dropwise addition of 5 N hydrochloric acid. Thereafter, the mixture is stirred at room temperature for an hour and then the by-product sulfur formed in small amount is filtered off. To the filtrate is added 50 ml of benzene, followed by neutralization with aqueous sodium hydroxide under cooling. The benzene layer is separated, dried over anhydrous sodium sulfate and concentrated under reduced pressure. The residue is subjected to silica gel column chromatography using chloroform-methanol (40:1 volume/volume) or benzene-methanol (95:5 volume/volume) as the developing solvent. Upon addition of an anhydrous oxalic acid-saturated ether solution to the thus-obtained product, white crystals of 5-dimethylamino-1,2,3-trithiane, precipitate. These are collected by filtration and dried to give the title compound as colorless plates.

Crop: 10.7 g.
Yield: 79.1%.
m.p 124°–125° C. (decomp.).

From further eluted fractions, 2.2 g of crude 4-(N,N-dimethylamino)-1,2-dithiolane is recovered. To the thus obtained compound is added a mixture of 1.8 g of oxalic acid in 10 ml of ethanol, and the resulting precipitates are collected by filtration to give the oxalate of 4-(N,N-dimethylamino)-1,2-dithiolane.

According to the same procedure as Reference Example 1 and described above, from the oxalate of 4-(N,N-dimethylamino)-1,2-dithiolane recovered, 2.0 g of the title compound is obtained. m.p. 124°–125° C. (decomp.)

EXAMPLE 2

Production of 5-dimethylamino-1,2,3-trithiane oxalate

Water (50 ml) is added to 10.09 g (0.05 mole) of 4-(N,N-dimethylamino)1,2-dithiolane-1-oxide hydrochloride. While maintaining the reaction temperature at 5° C., hydrogen sulfide gas is introduced into the solution until its amount reaches 90% of equimolar amount per 4-(N,N-dimethylamino)-1,2-dithiolane-1-oxide hydrochloride. The precipitated sulfur farmed in a small amount is filtered off.

Thereafter, the filtrate is treated in the same manner as Example 1 to give 5-dimethylamino-1,2,3-trithiane oxalate.

Crop: 10.2 g.
Yield: 75.0%.
m.p. 124°–125° C.

EXAMPLE 3

In accordance with the same procedure as Example 1 or 2, the following 1,2,3-trithiane compounds are produced. General formula

| $R_1$ $\diagdown$ $\diagup$ $R_2$ N— | Salt-forming acid | Yield (%) | m.p. (°C.) |
|---|---|---|---|
| CH$_3$ $\diagdown$ $\diagup$ CH$_3$ N— | HCl | 75 | 176–177 |
| CH$_3$CH$_2$ $\diagdown$ $\diagup$ CH$_3$CH$_2$ N— | (COOH)$_2$ | 73 | 125–126 |
|  | (COOH)$_2$ | 74 | 160–170 |
|  | (COOH)$_2$ | 70 | 165–166 |
| ☐N— | (COOH)$_2$ | 76 | 172 (decomp.) |

EXAMPLE 4

Production of 5-dimethylamino-1,2,3-trithiane oxalate

To a stirred aqueous solution (37.2 g) containing 9.2 g (0.05 mole) of 4-(N,N-dimethylamino)-1,2-dithiolane hydrochloride, is added dropwise 5.78 g (0.051 mole) of 30% aqueous hydrogen peroxide over about an hour, while maintaining the temperature of the reaction mixture at 10° C. Then, while maintaining the solution temperature of the reaction mixture at 5° C., the pH value is adjusted to 2 with aqueous sodium hydroxide, followed by dropwise addition of aqueous sodium sulfide (a solution of 11.71 g (0.049 mole) of sodium sulfide nonahydrate in 20 ml of water) over about an hour while maintaining the pH value at 2 to 3 with 5 N hydrochloric acid. Thereafter, the mixture is stirred at room temperature for an hour. The sulfur formed in a small amount is filtered off. The filtrate is treated in the same manner as Example 1 to give the title compound.

Crop: 10.46 g.
Yield 77.1%.
m.p. 124°–125° C.

What is claimed is:

1. A process for producing a 1,2,3-trithiane compound of the formula:

$$\begin{array}{c} R_1 \\ \diagdown \\ \diagup \\ R_2 \end{array} N-CH \begin{array}{c} CH_2-S \\ | \\ | \\ CH_2-S \end{array} S \qquad (I)$$

wherein each of $R_1$ and $R_2$ is independently alkyl of 1 4 carbon atoms, or alternatively, $R_1$ and $R_2$ together with the adjacent nitrogen atom form a 5- or 6-membered heterocyclic group which may further contain an oxygen, sulfur or nitrogen atom, or a salt thereof, which comprises (1) reacting a compound of the formula:

$$\begin{array}{c} R_1 \\ \diagdown \\ \diagup \\ R_2 \end{array} N-CH \begin{array}{c} CH_2-S \\ | \\ | \\ CH_2-S=O \end{array} \qquad (III)$$

wherein $R_1$ and $R_2$ are as defined above, or a salt thereof, with a compound of the formula:

Me$_2$S  (II)

wherein Me is hydrogen, an alkali metal atom or an ammonium radical, under an acid condition, (2) oxidizing the resulting by-product compound of the formula:

$$\begin{array}{c} R_1 \\ \diagdown \\ \diagup \\ R_2 \end{array} N-CH \begin{array}{c} CH_2-S \\ | \\ | \\ CH_2-S \end{array} \qquad (IV)$$

wherein $R_1$ and $R_2$ are as defined above, or a salt thereof, and (3) reacting the resulting compound (III), or a salt thereof, with the compound (II) under an acid condition to produce the compound (I), or a salt thereof.

2. A process as cliamed in claim 1, wherein each of $R_1$ and $R_2$ is methyl.

3. A process as claimed in claim 1, wherein the acid condition is pH 5 or below.

* * * * *